US010905128B2

(12) United States Patent
Mulaw et al.

(10) Patent No.: US 10,905,128 B2
(45) Date of Patent: Feb. 2, 2021

(54) TRICHODERMA COMPOSITIONS AND METHODS OF USING THE SAME

(71) Applicant: THE BOARD OF TRUSTEES OF THE UNIVERSITY OF ARKANSAS, Little Rock, AR (US)

(72) Inventors: Temesgen Mulaw, Stuttgart, AR (US); Yeshi Wamishe, Stuttgart, AR (US)

(73) Assignee: THE BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 0 days.

(21) Appl. No.: 16/270,834

(22) Filed: Feb. 8, 2019

(65) Prior Publication Data
US 2019/0246648 A1 Aug. 15, 2019

Related U.S. Application Data

(60) Provisional application No. 62/631,293, filed on Feb. 15, 2018.

(51) Int. Cl.
*A01N 63/30* (2020.01)
*A01N 63/38* (2020.01)
*C12R 1/885* (2006.01)

(52) U.S. Cl.
CPC .............. *A01N 63/30* (2020.01); *C12R 1/885* (2013.01); *A01N 63/38* (2020.01)

(58) Field of Classification Search
None
See application file for complete search history.

(56) References Cited

PUBLICATIONS

Abd-El-Moity TH, et al, 1981. Biological control of white rot disease of onion (*Sclerotium cepivorum*) by Trichoderma harzianum. Phytopathologische Zeitshrift 100, 29-35.
Abd-El-Moity TH, et al, 1983. Induction of new isolates of Trichoderma harzianum tolerant to © 2002 BSPP Plant Pathology (2002) 51, 735-745 744 J. P. Clarkson et al. fungicides and their experimental use for control of white rot of onion. Phytopathology 72, 396-400.
Benitez, T., et al. 2004. Biocontrol mechanism of Trichoderma strains. International Microbiol., 7: 249-260.
Chet. I. et al., 1981. Isolation and biocontrol potential of Trichoderma hamatum from soil naturally suppressive of Rhizoctonia solani. Phytopathology 71, 286-290.
Elad Y. 2000. Trichoderma harzianum T39 preparation for biocontrol of plant disease-control of Botrytis cinerea, Sclerotinia sclerotiorum and Cladosporium flavum. Biocontrol Sci Techn; 10: 499-507.
Elad, Y., et al. 1982. Control of Rhizoctonia solani in cotton by seed-coating with *Trichoderma* spp. spores. Plant Soil 66:279-281.
Hadar Y, et al. 1984. Evaluation of Trichoderma Koningii and T. hamatum from New York for biological control of seed rot caused by *Pythium* spp. Phytopathology, 74: 106-110.
Harman GE. 2000. Myths and dogmas of biocontrol: changes in perceptions derived from research on Trichoderma harzianum T-22. Plant Dis; 84(4): 377-393.
Harman, G.E. et al. 1983. Biological control of *Pythium* species. Seed Sci. Technol. 11:893-906.
Marois J.J., et al. 1982. Biological control of Verticillium wilt of eggplant in the field. Plant Disease 66, 1166-1168.
Mulaw T.B., et al. 2013. Novel endophytic *Trichoderma* spp. Isolated from Coffea arabica root are capable to controlling coffee tracheomycosis. Diversity 5: 750-766.
Mysore, V.T.; et al. 2005. Endophytic fungal assemblages from inner and twig of Terminalia arjuna W. and A. (Combretaceae). World J. Microbiol. Biotechnol, 21, 1535-1540.
Ohr HD; et al, 1973. The interaction of *Armillaria mellea* and *Trichoderma* spp. as modified by methyl bromide. Phytopathology, 63(8):965-973.
Paulitz T C. 2000 Population dynamics of biocontrol agents and pathogens in soil and rhizospheres. Eur J Plant Pathol; 106:401-413.
Ruppel, E.G., et al. 1983. Field tests of Trichoderma harzianum as a biocontrol agent of seedling disease in several crops and Rhizoctonia root rot of sugar beet. Crop Protection 2:399-408.
Sivan, A., et al. 1984. Biological control of Pythium aphanidermatum by a new isolate of Trichoderma harzianum. Phytopathology 74:498-501.

*Primary Examiner* — Medina A Ibrahim
(74) *Attorney, Agent, or Firm* — Quarles & Brady LLP (57) ABSTRACT

Provided herein is a *Trichoderma* strain designated as TM17 and deposited under accession number NRRL 67984. The *Trichoderma* strain TM17 and a carrier may be used to make agricultural compositions. Plants comprising the *Trichoderma* strain TM17 or the agricultural compositions provided herein are also contemplated. Methods for inhibiting the growth of a microorganism on a plant are also provided and may include contacting the plant with an effective amount of the *Trichoderma* strain TM17 or agricultural compositions including the *Trichoderma* strain TM17 to inhibit the growth of the microorganism on the plant.

13 Claims, 7 Drawing Sheets

TRICHODERMA COMPOSITIONS AND METHODS OF USING THE SAME

CROSS-REFERENCE TO RELATED APPLICATIONS

This patent application claims the benefit of priority of U.S. Provisional Patent Application No. 62/631,293, filed Feb. 15, 2018, which is incorporated herein by reference in its entirety.

BACKGROUND

Blast and sheath blight diseases of rice as well as other plant diseases are caused by two known fungal pathogens, namely *Magnaporthe oryzae* and *Rhizoctonia solani*. They are widespread and economically important problems of rice production in southern rice producing states of the USA and worldwide. Historically, these two diseases have been the most common biological causes of yield loss in Arkansas and some popular higher yielding rice varieties have been removed from production due in particular to blast disease. Moreover, development of resistance to current commercial fungicides is of great concern. A large acreage of rice is sprayed with fungicides every year. Besides, use of chemicals for crop diseases suppression is environmentally unsafe. Therefore, the major base reason to look for alternatives, particularly biocontrol agents, is to minimize risk of resistance development to fungicides and to minimize the use of chemicals. No single approach to control blast or sheath blight has been proven reliable. Hence, growers have been advised to adopt an integrated or additive disease management strategy such as combinations of matching fields with varieties, adequate field management, use of different levels of varietal resistance and chemical treatments. Replacement or reduction of chemical fungicides has been achieved in some crops through the use of biological fungicides based on the definition of Biological Control as proposed by Cook and Baker (1983). "Biological control is the reduction of the amount of inoculum or disease-producing activity of a pathogen accomplished by or through one or more organism other than man". This broad definition includes use of less virulent variants of the pathogen, more resistant cultivars of the host, and microbial antagonists or competitors "that interfere with the survival or disease-producing activities of a pathogen population."

Detailed evaluation of the environmental interactions is required to use such Biocontrol Agents (BCAs). Environmental conditions affect not only the survival of BCAs, but also their efficacy against pathogens (Paulitz, 2000). BCAs that are more flexible in terms of environmental adaptation can be more easily developed into commercial products, as their applications and target markets can be wider than those requiring specific environmental conditions. Species of *Trichoderma* have been shown to provide varying levels of biological control in a number of important plant pathogens, including *Sclerotium cepivorum* (Abd-el Moity et al, 1983, Abd-el Moity et al, 1981), *Armillaria mellea* (Ohr et al, 1973), *Rhizoctonia solani* (Chet et al, 1981, Elad et al, 1982, Ruppel et al, 1983), *Verticillium dahliae* (Jordan et al, 1978, Marios et al, 1982) and *Pythium* spp. (Chet et al, 1981, Hadar et al, 1984, Harman et al, 1983, Sivan et al, 1984). However, to date there have been no concerted efforts made to use these fungi to control plant diseases caused by *Magnaporthe oryzae* and *Rhizoctonia solani*. These diseases are more severe in high input agriculture such as the USA rice production system. The *Trichoderma*-plant interactions are complex. An important fact is that different strains substantially vary in their effects on plants. *Trichoderma* strains have been already used as biocontrol agents against numerous plant pathogens and quite a few have been developed for use in commercial production. For instance, *Trichoderma harzianum*, known as Trichodex®) is on use as biocontrol product for field and greenhouse crops (Elad, 2000; Harman, 2000). However, a great variability exists in terms of biocontrol activity, specificity, mechanism of action, production of metabolites and survival in soil or on plants among *Trichoderma* species and hence, their use as BCAs can be different (Benitez et al., 2004). Thus, there remains a need in the art for new BCAs that can be used to control devastating plant diseases caused by, for example, *Magnaporthe oryzae* and *Rhizoctonia solani*.

SUMMARY

In one aspect of the present invention, a new *Trichoderma* strain designated as TM17 and deposited under accession number NRRL 67984 is provided.

In another aspect, the present invention relates to agricultural compositions. The agricultural compositions may include *Trichoderma* strain TM17 and a carrier.

In a further aspect of the present invention, plants are provided. The plants may include *Trichoderma* strain TM17 or any one of the agricultural compositions described herein. The *Trichoderma* strain TM17 or any one of the agricultural compositions described herein may be present on or within at least a part of the plant.

In a still further aspect of the present invention, methods for inhibiting the growth of a microorganism on a plant are provided. The methods may include contacting the plant with an effective amount of *Trichoderma* strain TM17 or any one of the agricultural compositions described herein to inhibit the growth of the microorganism on the plant. The plant may be a rice plant and the microorganism may be a fungi. The plant may be contacted by foliage spray application of the agricultural compositions or the *Trichoderma* strain TM17.

BRIEF DESCRIPTION OF DRAWINGS

FIGS. 2A-2D show the dual confrontation result of TM17 against *Magnaporthe oryzae*, FIGS. 2A, 2B, 2C, and 2D are day 3, 4, 6, and 10, respectively. BL-Blast pathogen (*Magnaporthe oryzae*), TR (*Trichoderma* sp.-TM17) and TR+BL=dual plate for TR and BL in a single plate.

FIGS. 3A-3C show the dual confrontation result of TM17 against *Rhizoctonia solani* AG1-1A. FIGS. 3A, 3B, 3C are day 3, 4, 6, respectively. SB-Sheath blight (*Rhizoctonia solani* AG1-1A), TR-*Trichoderma* sp.-(TM17) and TR+SB=dual plate for TR and SB in a single plate.

FIGS. 5A-5D show the performance of rice plants treated in accordance with the present invention.

DETAILED DESCRIPTION

Here, in the non-limiting Examples, the present inventors have identified a *Trichoderma* strain (referred to as "TM17") that may be applied to plants to suppress the growth of microbial plant pathogens such as *Magnaporthe oryzae* and *Rhizoctonia solani*. Without being bound by theory, the present inventors show in the non-limiting Examples that spraying plants with TM17 allows TM17 to colonize the plant surface thereby creating a plant-*Trichoderma* interaction system. The plant-*Trichoderma* interaction system protects the plants from being colonized by, and damaged by, pathogenic microbes such as fungi. Given this data, the present inventors show that TM17 may provide a broad-spectrum control of multiple diseases in plants and provide a safe alternative to chemical pesticides.

In one aspect of the present invention, a new *Trichoderma* strain designated as TM17 is provided. A viable culture of TM17 has been deposited in the ARS Culture Collection (NRRL), Peoria, Ill. under the accession number NRRL 67984. *Trichoderma* strain TM17 produces abundant spores and has been shown to suppress and control the rice blast and sheath blight diseases caused by *Magnaporthe oryzae* and *Rhizoctonia solani* AG1-1A, respectively. The present invention relates to a method of protecting plants from infection, which comprises contacting the plant with *Trichoderma* strain TM17 under conditions effective for the *Trichoderma* strain to colonize the surface of the plant, thereby creating a plant-*Trichoderma* interaction system. A biologically pure culture of fungus *Trichoderma* sp. isolate TM17 for inducing suppression of rice plant diseases caused by *Magnaporthe oryzae* and *Rhizoctonia solani* AG1-1A is provided. The culture produces abundant mycelium, conidia and chlamydospores.

In another aspect, the present invention relates to agricultural compositions. An "agricultural composition" is a composition formulated for application to a plant or plant part. An agricultural composition is commonly in liquid form for application by spraying or soaking, but may be in a solid, granular, or powder form for rehydration or application by dusting or dry coating. The agricultural composition may be concentrated for dilution in water or other solvent.

The agricultural compositions may include *Trichoderma* strain TM17 and a carrier. As used herein, a "carrier" may be solid or liquid and may include substances ordinarily employed in formulations applied to plants. Carriers may include a buffer, water, oil, nonionic surfactants, ionic surfactants such as cationic or anionic surfactants, or available agricultural byproducts from, for example and without limitation, rice.

In some embodiments, the agricultural compositions may also include an additional active ingredient such as, without limitation, a fungicide, an herbicide, a biosanitizer product or fertilizer.

The agricultural compositions may include *Trichoderma* strain TM17 at a concentration between $10^5$ to $10^{12}$ or more conidia per milliliter or any range therein. Suitably, the concentration of the *Trichoderma* strain TM17 in the agricultural composition may be $10^7$ to $10^{10}$ conidia per milliliter. As detailed in the Examples, the concentration of *Trichoderma* strain TM17 conidia in the agricultural composition may be quantified using a hemocytometer.

In a further aspect of the present invention, plants are provided. The plants may include *Trichoderma* strain TM17 or any one of the agricultural compositions described herein. The *Trichoderma* strain TM17 or any one of the agricultural compositions described herein may be present on or within at least a part of the plant.

As used herein, a "plant" includes any portion of the plant including, without limitation, a whole plant or a portion of a plant such as a part of a root, leaf, stem, seed, pod, flower, cell, tissue plant germplasm, asexual propagate, or any progeny thereof. For example, a rice plant refers to the whole rice plant or portions thereof including, without limitation, the leaves, roots, or otherwise. Suitable "plants" may include, without limitation, a rice plant, a cotton plant, a soybean plant, a wheat plant, a sorghum plant, or a corn plant. In some embodiments, the plant is a rice plant.

In a further aspect of the present invention, methods for inhibiting the growth of a microorganism on a plant are provided. The methods may include contacting the plant with an effective amount of *Trichoderma* strain TM17 or any one of the agricultural compositions described herein to inhibit the growth of the microorganism on the plant.

The "microorganism" may be any bacterial or fungal plant pathogen. Suitably, the microorganism may be a fungal plant pathogen including, without limitation, a *Magnaporthe* species or a *Rhizoctonia* species. In some embodiments, the microorganism is *Magnaporthe oryzae* or *Rhizoctonia solani*. The *Rhizoctonia solani* may be *Rhizoctonia solani* AG1-1A. *Magnaporthe oryzae* is the causative agent of blast disease in rice and *Rhizoctonia solani* AG1-1A is the causative agent of sheath blight.

As used herein, "contacting" may be carried out through any of the variety of procedures used to apply compositions to plants that will be apparent to the skilled artisan. Suitable application methods may include, without limitation spraying or dusting. Other suitable application procedures can be envisioned by those skilled in the art. Contacting may also be carried out indirectly via application, for example, to the soil surrounding a plant, trunk injection, or other plant media or substrates. The "contacting" of the present methods may be carried out before or after the microorganism grows on the plant.

In the present methods, various parts of the plant may be contacted with or by *Trichoderma* strain TM17 or any one of the agricultural compositions described herein. Suitably and without limitation, the leaves or seeds of the plant may be contacted with *Trichoderma* strain TM17 or any one of the agricultural compositions described herein.

In some embodiments, the plant may be contacted at least 2, 3, 4, 5, or more times with with *Trichoderma* strain TM17 or any one of the agricultural compositions described herein during a single growing season. Different parts of the plant may be contacted at different points within the growing season. The plant may be contacted with the *Trichoderma* strain TM17 or the agricultural compositions using different formulations or means of contacting at different points within a growing season.

"Effective amount" is intended to mean an amount of a composition described herein sufficient to inhibit the growth of a microorganism on a plant by, for example, 10%, 20%, 50%, 75%, 80%, 90%, 95%, or 1-fold, 3-fold, 5-fold, 10-fold, 20-fold, or more compared to a negative control plant not treated with the *Trichoderma* strain TM17 or one of the agricultural compositions provided herein. In some embodiments, the effective amount of *Trichoderma* strain TM17 either alone or in an agricultural composition may be $10^5$ to $10^{12}$ or more conidia per milliliter or any range therein. Suitably, the concentration of *Trichoderma* strain TM17 either alone or in an agricultural composition is $10^7$ to $10^{10}$ conidia per milliliter. A "negative control" refers to a sample that serves as a reference for comparison to a test sample. For example, a test sample can be taken from a test condition including the presence of *Trichoderma* strain TM17 and compared to negative control samples lacking *Trichoderma* strain TM17 or including a composition not expected to inhibit microbial growth. One of skill in the art will recognize that controls can be designed for assessment of any number of parameters.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Isolation of *Trichoderma* sp. TM17

Although the concept of biological control of plant diseases has been known for a number of years, the idea of selecting endophytic biological control agents is relatively new. In fact, *Trichoderma* sp.-TM17 is the first microorganism isolated from rice seed as an endophyte that showed a potential to control both Blast and Sheath blight disease of rice in Arkansas.

Figure 1:
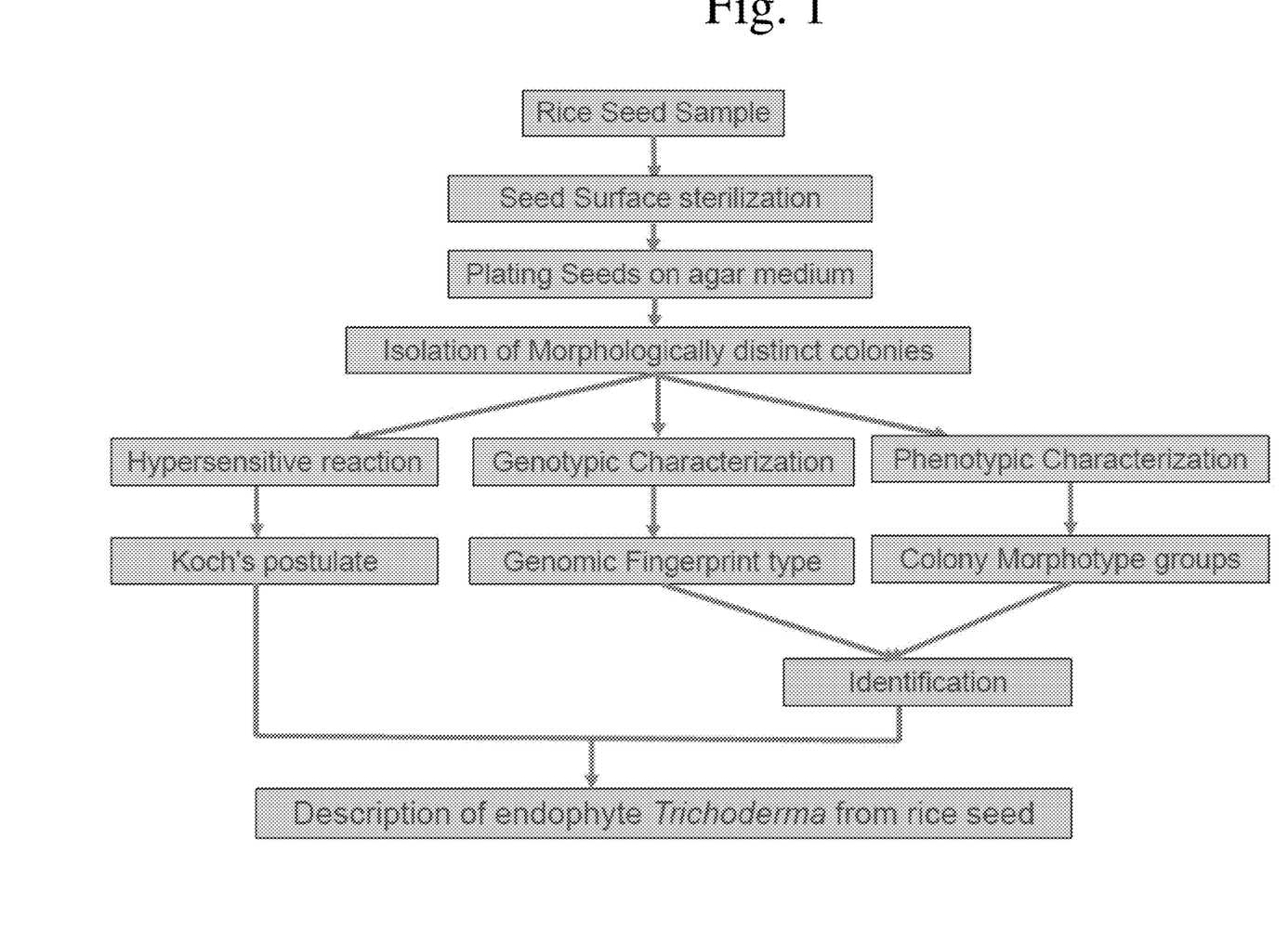
FIG. 1 shows the methodology used to isolate, characterize and the final identification protocol for the endophyte *Trichoderma* sp. TM17.
Figure 2A:
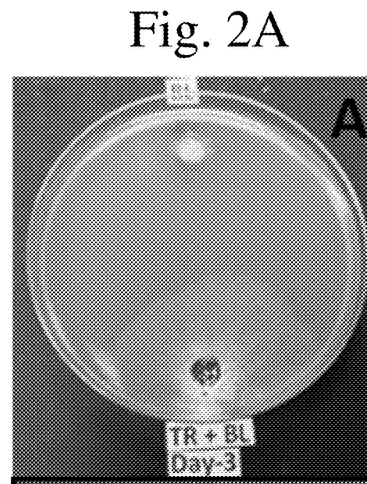
Figure 2B:
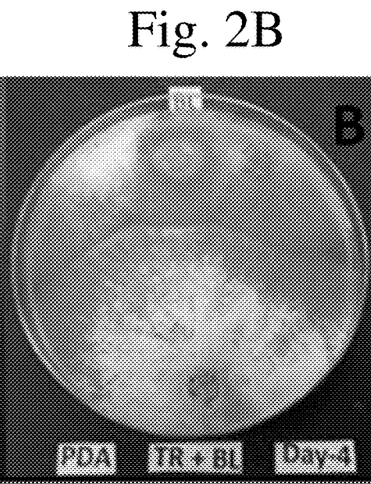
Figure 2C:
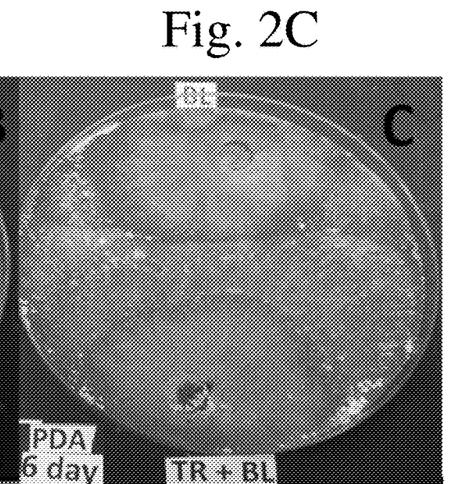
Figure 2D:
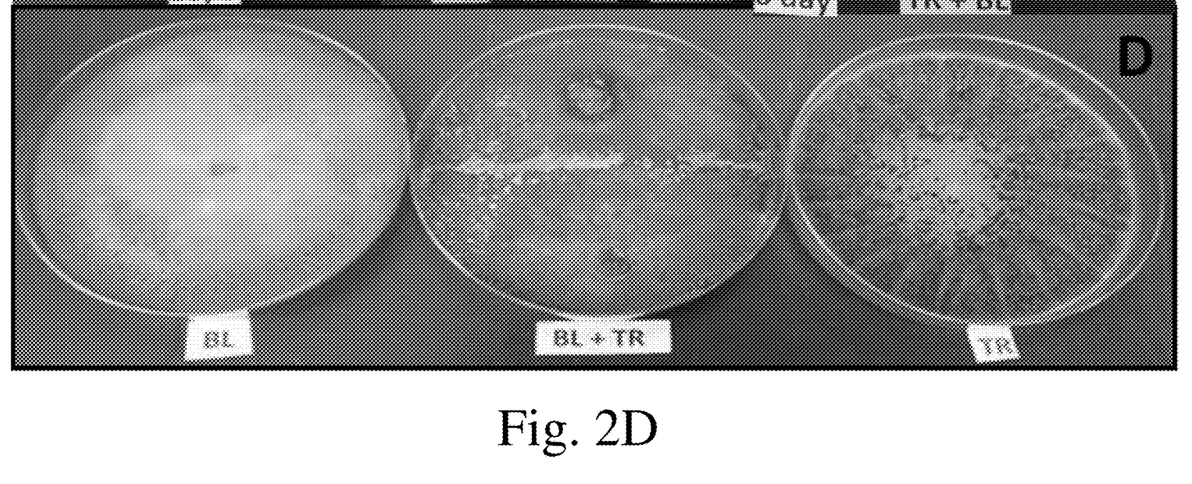
Figure 3A:
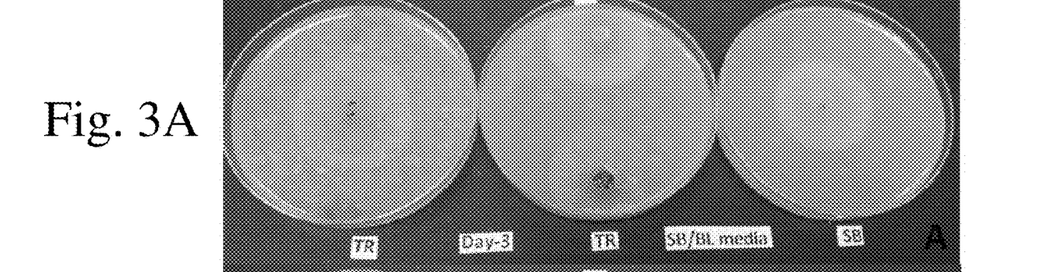
Figure 3B:
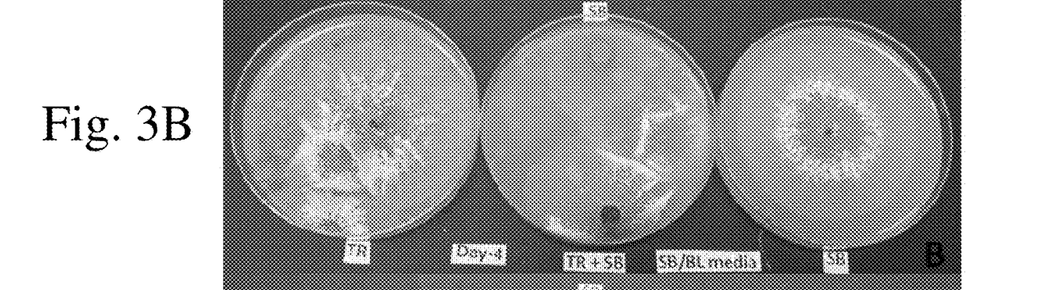
Figure 3C:
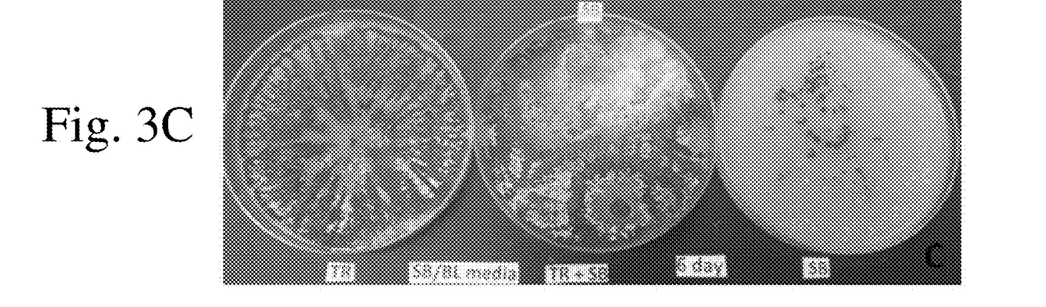
Figure 4:
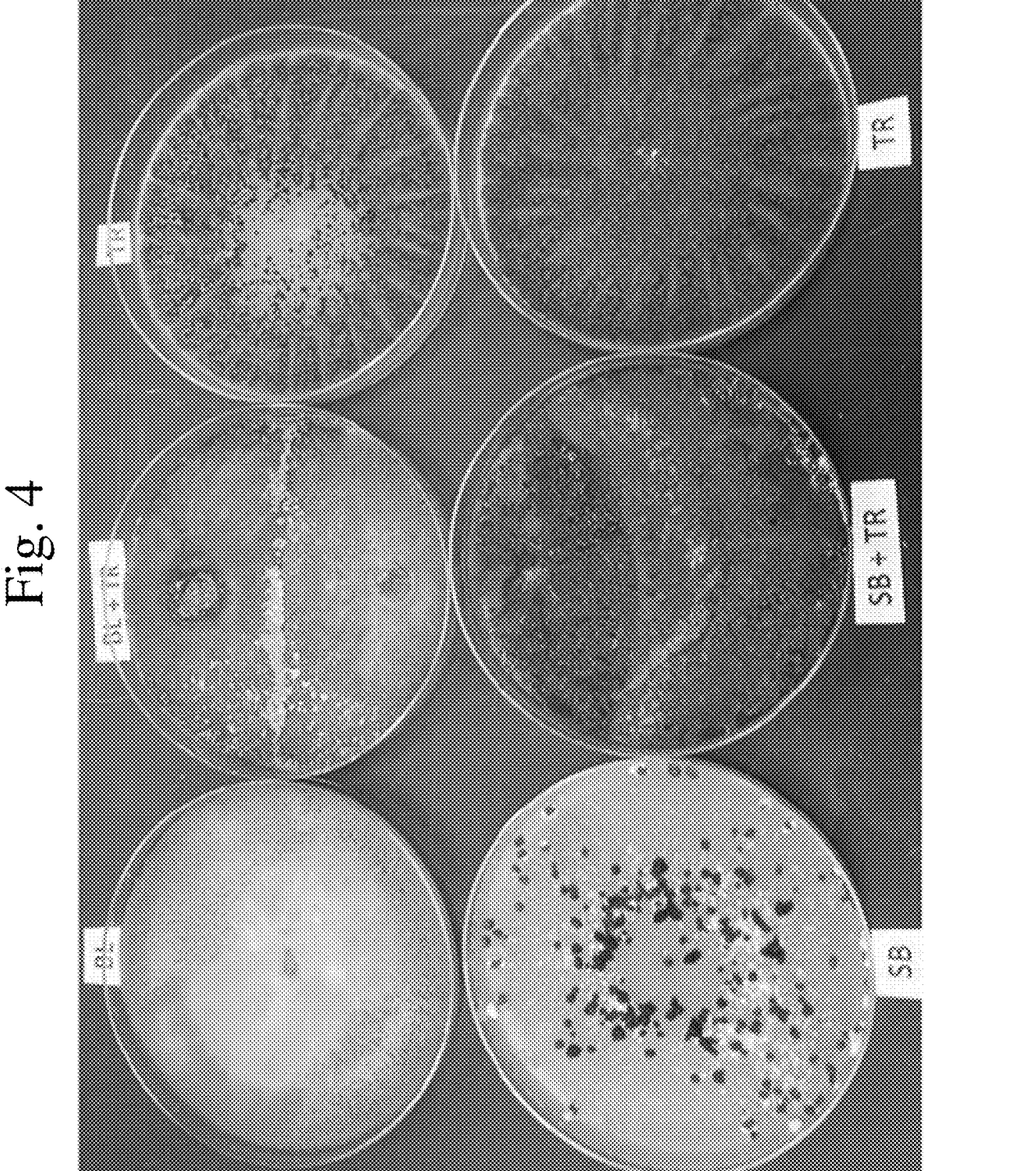
FIG. 4 shows the growth performance of BL, SB, TR and dual inoculated plates after 10 days of inoculation.

The *Trichoderma* strain disclosed herein, *Trichoderma* sp.-TM17, was isolated from rice seed as an endophyte. The isolation of the endophytic strain was accomplished by the following procedure. See, e.g., FIG. 1. Rice seeds were collected from different sites of major rice growing fields of Arkansas at rice crop maturity and were kept in paper bags at 4° C. until use. Seed samples randomly selected from the mixed samples were set for processing for the test. Isolation of endophyte fungi was according to the protocol of Mysore et al. 2005. Briefly, seeds were cleaned under running tap water to remove debris and then air-dried on a sterile filter paper. From each sample, seeds were surface-sterilized by immersing them in 95% ethanol (2 min), followed by sodium hypochlorite (4% available chlorine; 5 min), and were then washed three times with sterile water. Samples were then allowed to dry on a sterile filter paper for 10 min in a sterile laminar flow chamber. Seeds were plated horizontally on potato dextrose agar (PDA) supplemented with streptomycin sulphate (0.4 mg/mL). In a course of 5 days incubation at 25° C., individual hyphal tips of the developing colonies were re-plated onto PDA plates and were further incubated for 8-10 days. Eventually, single spore cultures for each strain were prepared to assure sample purity. Isolates are currently stored in 30% glycerol at −80° C. in the Collection of Plant Pathology at Rice Research and Extension Center (RREC).

Example 2—Preparation of TM17 Samples for Experimentation

Conidia and mycelia of TM17 were produced by growing the isolate on PDA agar for 7 days under continuous fluorescent light at room temperature. Conidia were removed from the agar surface by pipetting 5 ml of sterile distilled water on the surface and gently rubbing the surface with a sterile cotton-tipped applicator. Conidia were counted in a hemocytometer, and the suspensions adjusted with water to provide the desired concentration of conidia in each test. There were five replications in all experiments, and each experiment was done twice.

Example 3—Biocontrol Activity of TM17 In Vitro

Biocontrol activities of *Trichoderma* sp. strain TM17 against the two fungal rice pathogens were determined in vitro on potato dextrose agar (PDA) (20 ml/plate). See FIGS. 2A-2D, 3A-3C, and 4. The two pathogens were *Magnaporthe oryzae* (FIGS. 2A-2D and 4) and *Rhizoctonia solani* AG1-1A (FIGS. 3A-3C and 4). A plug of the biocontrol agent (8 mm diameter) from the edge of 5-day old colonies of the *Trichoderma* cultures and of 10-day old colonies of the pathogens were paired on the medium on opposite sides of 9×1.5 cm petri plates and then were incubated at room temperature. Also fresh culture agar plugs of prey and predator fungi were placed on a PDA plate on opposite poles, each, 1 cm away from the edge of the plate. The disks from TM17 were placed 5 cm from those of the pathogens. Isolates of *Magnaporthe oryzae* and *Rhizoctonia solani* were placed on the agar 48 hours before TM17. All other combinations were done simultaneously. Cultures were incubated at room temperature under continuous fluorescent light of the same intensity and monitored for inhibition every day from 3 to 10 days after placement of the TM17. Antagonistic potential was estimated as a reduction of the prey growth rate corrected for the growth rate of a prey when confronted with itself. Antagonistic potential presented as averaged growth inhibition or overgrowth of each plant pathogen (prey) by *Trichoderma* strain TM17 and was expressed in percentages. In both cases 100% represented unrestricted growth of the prey corrected for the confrontation with itself. *Trichoderma* sp.-TM17 showed an aggressive biocontrol potential growing faster and eventually overwhelming the tested pathogen isolates compared to the control plates inoculated with the respective pathogen alone under the same conditions of incubation. The *Trichoderma* sp.-TM17 did not produce zones of inhibition against any of the pathogens on plates. However, its competitive growth overwhelmed the pathogen growth. See FIGS. 2A-2D, 3A-3C, and 4.

Example 4—Biocontrol Activity of TM17 In Vivo

Figure 7A:
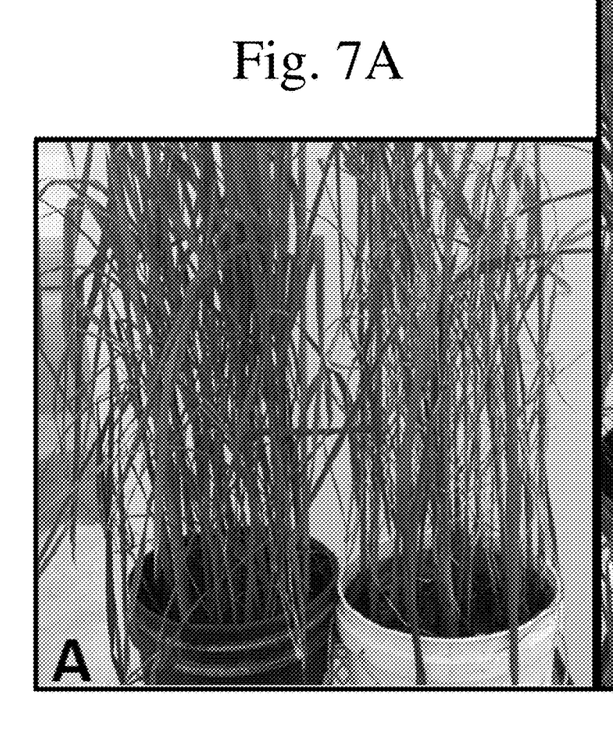
FIGS. 7A and 7B show two photographs to demonstrate the contrast between TM17 treated and untreated rice plants from two different views. The plants on the left of each picture were inoculated with *Rhizoctonia solani* AG1-1A agar plugs 24 h after TM17 treatment and the plants on the right were inoculated with *Rhizoctonia solani* AG1-1A agar plugs, but not treated with TM17.
Figure 7B:
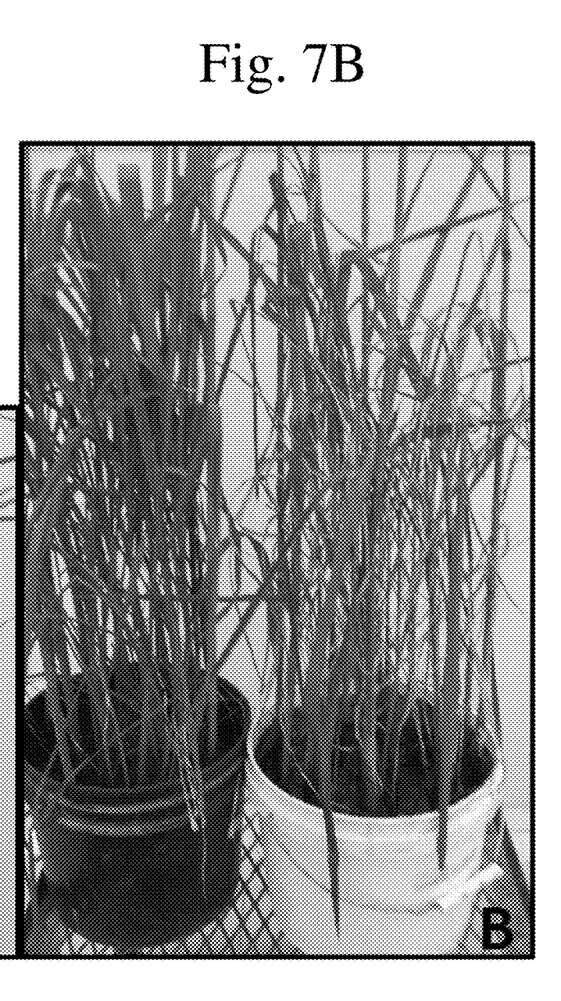

The ability of *Trichoderma* sp.-TM17 to suppress diseases was also determined in vivo. This endophyte *Trichoderma* isolate revealed high inhibition potential on the growth of the two prey isolates. Greenhouse experiments were carried out for both blast (FIGS. 5A-5D, FIG. 6) and sheath blight (FIGS. 7A-7B) control by TM17. To test for blast, seeds of M2O6 planted in hill plots in a 0.02 m² flat containing greenhouse soil:sand:loam mixture in 3:1:1 proportion, respectively. There were 81 hill plots in a flat. The flats were kept in the greenhouse at an average temperature of 78° F. and 85% relative humidity. Flats were watered for 3 weeks and fertilized as needed. Conidia of TM17 harvested from 8 to 10-day-old cultures growing on PDA were washed off using cotton-tipped applicator. Suspensions of conidia were counted using a hemocytometer and adjusted to contain $10^9$ conidia per milliliter for spray application.

To test for sheath blight, 10 to 15 seeds were planted in a half-gallon pot, watered, and fertilized as needed. After a month, sheath blight disease causing pathogen *Rhizoctonia solani* AG1-1A was grown on PDA plates. For pre-inoculation treatment, TM17 was sprayed on rice seedlings at full tillering developmental stage and then after 24 hours the plants were inoculated following standard greenhouse procedure by placing 10 days old mycelial agar plugs of *Rhizoctonia solani* AG1-1A at the base of each culm. For post-inoculation treatment, rice of similar age were inoculated using mycelial agar plugs in a similar way except TM17 was sprayed 24 hours after inoculation at a concentration of $10^9$ conidia per ml. On the other hand, a conidial suspension of *M oryzae* was prepared by growing it on rice bran agar at 27° C. for 10 days, washed with sterilized distilled water and strained through sterile filter papers to remove mycelia. Conidial concentrations of *M oryzae* were adjusted to $10^5$ conidia per ml. Then the suspensions were kept at 4° C. until foliage spray. Similar to *Rhizoctonia solani* AG1-1A, for pre-inoculation treatment, TM17 was sprayed on rice seedlings at 24 h before spray-inoculation by *M oryzae* suspension. For post-inoculation treatment, rice seedlings of similar age were spray-inoculated with the spore suspension of *M oryzae* at 24 h before spraying with TM17 at $10^9$ conidia per ml.

Figure 5A:
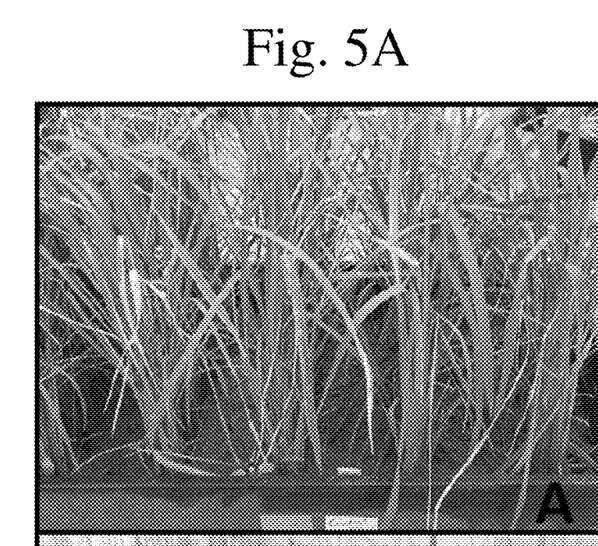
FIG. 5A shows control treatment that was inoculated with the blast pathogen but with no TM17 applied.
Figure 5B:
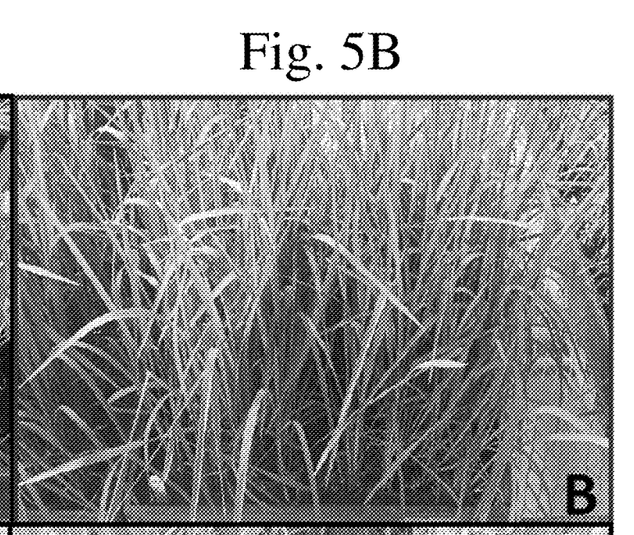
FIG. 5B shows plants pre-treated with TM17 and then inoculated with the blast pathogen.
Figure 5C:
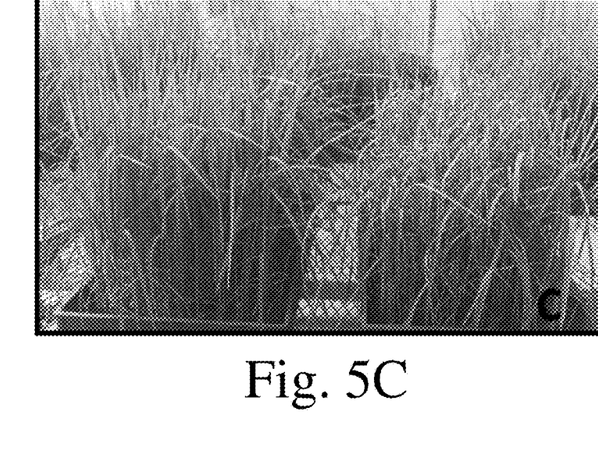
FIGS. 5C and 5D show inoculated plants but the healthy looking plants on the left are treated with TM17 prior to inoculation with the blast pathogen.
Figure 5D:
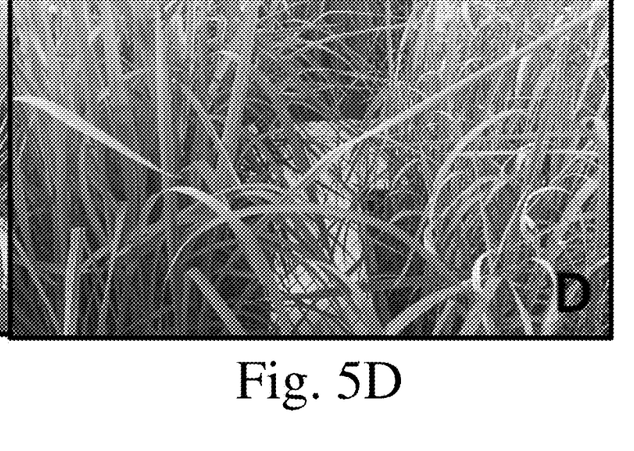
Figure 6:
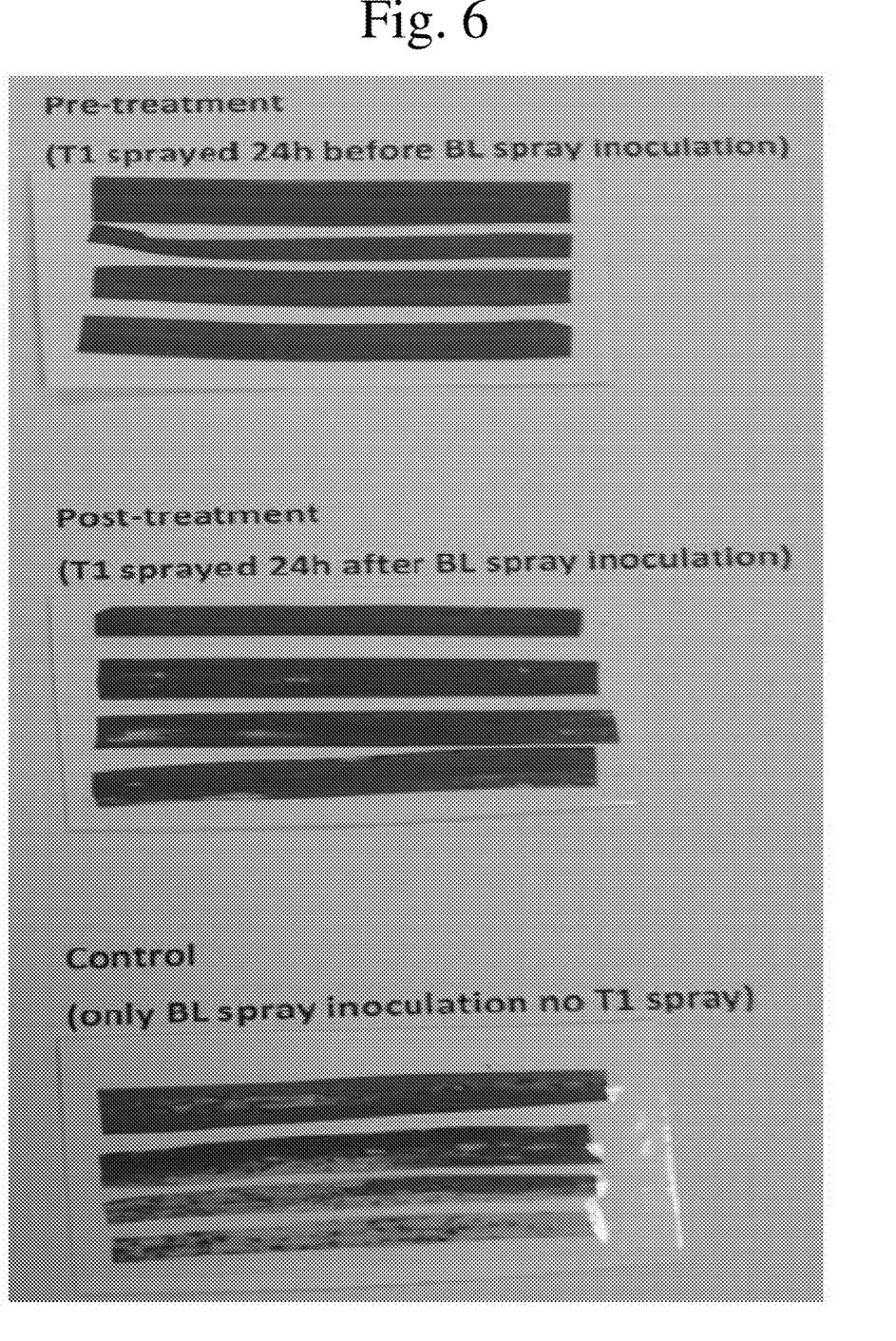
FIG. 6 shows the visible lesion size on the rice leaves. The top picture shows the results when TM17 is sprayed 24 h before inoculation with the blast pathogen. The middle picture shows the results of post-treatment with TM17. The TM17 was applied 48 h after the blast pathogen inoculation. The picture at the bottom shows the control plants inoculated with the blast pathogen and not treated with TM17.

Application of *Trichoderma* sp.-TM17:

Conidial suspension of TM17 was prepared for protective and therapeutic treatments. In the former, TM17 was sprayed 48 hours before inoculating the respective pathogens (FIGS. 5B-5C). In the latter rice plants were inoculated with isolates of *Magnaporthe oryzae* and *Rhizoctonia solani* AG1-1A, then 48 h after the rice plants were sprayed with TM17 suspension (FIGS. 5A-5B). Experimental controls were treated with water in place of TM17.

Data Collected:

The number of rice plants with blast lesions and without lesions were counted. For the sheath blight, the lengths of lesions were measured in proportion to height of the plant. This invention relates to *Trichoderma* sp.-TM17, which is seen potentially useful in controlling the two major rice diseases caused by *Magnaporthe oryzae* and *Rhizoctonia solani* AG1-1A. To suppress the blast and sheath blight rice diseases, TM17, a strain of *Trichoderma* sp. was applied to greenhouse grown rice plants in an amount sufficient to colonize and populate the plant surface, thereby reducing/suppressing the growth of the pathogens. See FIGS. 5A-5D, FIG. 6, and FIG. 7A-7B.

REFERENCES

Abd-El-Moity T H, Shatla M N, 1981. Biological control of white rot disease of onion (*Sclerotium cepivorum*) by *Trichoderma harzianum*. Phytopathologische Zeitshrift 100, 29-35.

Abd-El-Moity T H, Papavizas G C, Shatla M N, 1983. Induction of new isolates of *Trichoderma harzianum* tolerant to © 2002 BSPP Plant Pathology (2002) 51, 735-745 744 J. P. Clarkson et al. fungicides and their experimental use for control of white rot of onion. Phytopathology 72, 396-400.

Benitez, T., A. M. Rincon, M. C. Limon and A. C. Codon. 2004. Biocontrol mechanism of *Trichoderma* strains. International Microbiol., 7: 249-260.

CHET. I. & BAKER, P., 1981. Isolation and biocontrol potential of *Trichoderma hamatum* from soil naturally suppressive of *Rhizoctonia solani*. Phytopathology 71, 286-290.

Cook R, Baker K F. 1983. The nature and practice of biological control of plant pathogens. St Paul, M N, USA: The American Phytopathological Society.

Elad Y. 2000. *Trichoderma harzianum* T39 preparation for biocontrol of plant disease-control of *Botrytis cinerea, Sclerotinia sclerotiorum* and *Cladosporium flavum*. Biocontrol Sci Techn; 10: 499-507.

Elad, Y., Kalfon, A. and Chet, I. 1982. Control of *Rhizoctonia solani* in cotton by seed-coating with *Trichoderma* spp. spores. Plant Soil 66: 279-281.

Hadar Y, Harman G E, Taylor A G. 1984. Evaluation of *Trichoderma Koningii* and *T hamatum* from New York for biological control of seed rot caused by *Pythium* spp. Phytopathology, 74: 106-110.

Harman G E. 2000. Myths and dogmas of biocontrol: changes in perceptions derived from research on *Trichoderma harzianum* T-22. Plant Dis; 84(4): 377-393.

Harman, G. E. and Hadar, Y. 1983. Biological control of *Pythium* species. Seed Sci. Technol. 11:893-906.

Marois J. J., S. A. Jahnson, M. T. Dunn and G. C. Papavizas. 1982. Biological control of *Verticillium* wilt of eggplant in the field. Plant Disease 66, 1166-1168.

Mulaw T. B., Kubicek C. P. and Druzhinina I. S. 2013. Novel endophytic *Trichoderma* spp. Isolated from *Coffea arabica* root are capable to controlling coffee tracheomycosis. Diversity 5: 750-766.

Mysore, V. T.; Basavanna, M.; Monnanda, S. N.; Harishchandra, S. P.; Kukkundoor, R. K.; Ven, S.; Hunthrike, S. S. 2005. Endophytic fungal assemblages from inner and twig of Terminalia arjuna W. and A. (Combretaceae). World J. Microbiol. Biotechnol, 21, 1535-1540.

Ohr H D; Munnecke D E; Bricker J L, 1973. The interaction of *Armillaria mellea* and *Trichoderma* spp. as modified by methyl bromide. Phytopathology, 63(8):965-973

Paulitz T C. 2000 Population dynamics of biocontrol agents and pathogens in soil and rhizospheres. Eur J Plant Pathol; 106: 401-413.

Ruppel, E. G., R. Baker, G. E. Harman, J. P. Hubbard, R. J. Hecker and I. Chet. 1983. Field tests of *Trichoderma harzianum* as a biocontrol agent of seedling disease in several crops and *Rhizoctonia* root rot of sugar beet. Crop Protection 2:399-408.

Sivan, A., Y. Elad and I. Chet. 1984. Biological control of *Pythium aphanidermatum* by a new isolate of *Trichoderma harzianum*. Phytopathology 74:498-501.

DEPOSIT INFORMATION

A deposit of the University of Arkansas Division of Agriculture proprietary *Trichoderma* sp. strain designated as TM17 (RREC F21) disclosed above and recited in the appended claims has been made with the ARS Culture Collection (NRRL), 1815 N. University Street, Peoria, Ill. 61604. The date of deposit was Sep. 18, 2020. The deposit comprises 5 liquid nitrogen stocks, which were found viable on Sep. 18, 2020. All restrictions will be irrevocably removed upon granting of a patent, and the deposit is intended to meet all of the requirements of 37 C.F.R. §§ 1.801-1.809. The NRRL Accession Number is 67984. The deposit will be maintained in the depository for a period of thirty years, or five years after the last request, or for the enforceable life of the patent, whichever is longer, and will be replaced as necessary during that period.

We claim:

1. An agricultural composition comprising a *Trichoderma* strain designated as TM17 and a carrier comprising a buffer and/or agar, wherein the concentration of the *Trichoderma* is between $10^7$ to $10^{10}$ conidia per milliliter of the carrier, wherein the *Trichoderma* strain TM17 has been deposited under Accession number NRRL 67984; and where the agricultural composition is capable of suppressing growth of fungal blast and sheath blight diseases.

2. The agricultural composition of claim 1, wherein the agricultural composition is a liquid suspension.

3. A plant sprayed with the agricultural composition of claim 1, wherein the *Trichoderma* strain colonizes on the plant surface and inhibits growth of *Magnaporthe oryzae* and *Rhizoctonia solani* pathogens on the plant or parts thereof.

4. The plant of claim 3, wherein the *Trichoderma* strain colonizes on or within the leaves of the plant.

5. The plant of claim 3, wherein the plant is a rice plant.

6. A method for inhibiting the growth of fungal pathogens on a rice plant comprising contacting the rice plant with an effective amount of an agricultural composition comprising a *Trichoderma* strain designated as TM17 and a carrier comprising a buffer and/or agar, wherein the agricultural composition inhibits the growth of the fungal pathogens on the rice plant, wherein the fungal pathogens comprise *Magnaporthe oryzae* and *Rhizoctonia solani*; and wherein the *Trichoderma* strain TM17 has been deposited under accession number NRRL 67984.

7. The method of claim 6, wherein the contacting is carried out before the microorganism grows on the plant.

8. The method of claim 6, wherein the contacting is carried out after the microorganism grows on the plant.

9. The method of claim 6, wherein the contacting is carried out by spraying the plant with the composition.

10. The method of claim 6, wherein the contacting is carried out by dusting the plant with composition.

11. The method of claim 6, wherein the leaves of the plant are contacted with the composition.

12. The method of claim 6, wherein the seeds of the plant are contacted with the composition.

13. The method of claim 6, wherein the plant is contacted at least 2 times with the composition.

* * * * *